(12) United States Patent
Weyrauch et al.

(10) Patent No.: US 8,957,260 B2
(45) Date of Patent: Feb. 17, 2015

(54) PROCESS FOR THE OXIDATION OF MESITOL

(75) Inventors: Jan Philipp Weyrauch, Mannheim (DE); Vivien Ellinor Weyrauch, legal representative, Berlin (DE); Gunhild Weyrauch, legal representative, Oberursel (DE); Martine Weis, Mannheim (DE); Joaquim Henrique Teles, Waldsee (DE); Klaus Ebel, Lampertheim (DE); Peter Deglmann, Mannheim (DE)

(73) Assignee: BASF SE (DE)

( * ) Notice: Subject to any disclaimer, the term of this patent is extended or adjusted under 35 U.S.C. 154(b) by 183 days.

(21) Appl. No.: 13/364,532

(22) Filed: Feb. 2, 2012
(Under 37 CFR 1.47)

(65) Prior Publication Data
US 2012/0203013 A1    Aug. 9, 2012

Related U.S. Application Data

(60) Provisional application No. 61/439,966, filed on Feb. 7, 2011.

(51) Int. Cl.
*C07C 37/07* (2006.01)
*C07C 37/60* (2006.01)
*C07C 39/08* (2006.01)
*C07C 45/28* (2006.01)

(52) U.S. Cl.
CPC ............... *C07C 37/07* (2013.01); *C07C 45/28* (2013.01); *C07C 2101/16* (2013.01)
USPC .......................................... 568/771; 568/763

(58) Field of Classification Search
USPC .................................. 568/771, 763; 549/411
See application file for complete search history.

(56) References Cited

U.S. PATENT DOCUMENTS

| 3,957,887 | A | 5/1976 | Ichikawa et al. |
| 6,486,360 | B1 | 11/2002 | Aubry et al. |
| 6,956,137 | B1 | 10/2005 | Aubry et al. |
| 2004/0220416 | A1 | 11/2004 | Emsenhuber et al. |

FOREIGN PATENT DOCUMENTS

| AT | 413099 T | 11/2008 |
| DE | 2345062 A1 | 4/1974 |
| EP | 288337 A1 | 10/1988 |
| EP | 1403234 A2 | 3/2004 |
| WO | WO-0061524 A1 | 10/2000 |
| WO | WO-0064842 A1 | 11/2000 |
| WO | WO-2006108492 A1 | 10/2006 |
| WO | WO-2007042114 A1 | 4/2007 |

OTHER PUBLICATIONS

Aubry, J.M., "Search for Singlet Oxygen in the Decomposition of Hydrogen Peroxide by Mineral Compounds in Aqueous Solutions," J. Am. Chem. Soc., 107, 5844-5849, 1985.*
Nardello et al. "Slnglet Oxygen Generation from H2O2/MoO4: peroxidation of hydrophobic substrates in pure organic solvents," Tetrahedron Letters 43, 8731-8734, 2002.*
Carreno et al., "Oxidative de-aromatization of para-alkyl phenols into para-perosyquinols and para-quinols mediated by oxone as a source of singlet oxygen," Angew. Chemie. Int. Ed. 45, 2737-2741, 2006.*
Aubry, J. "Search for Singlet Oxygen in the Decomposition of Hydrogen Peroxide by Mineral Compounds in Aqueous Solutions" American Chemical Society (1985) pp. 5844-5849.
Nardello, V., et al. "Lanthanum(III)-Catalyzed Disproportionation of Hydrogen Peroxide: A Heterogeneous Generator of Singlet Molecular Oxygen—$^1O_2(^1A_g)$-in Near-Neutral Aqueous and Organic Media for Peroxidation of Electron-Rich Substrates" Chem. Eur. J. (2003) 9, No. 2, pp. 435-441.
Nardello, V., et al. "Singlet Oxygen Generation from $H_2O_2/MoO_4^{2-}$:peroxidation of hydrophobic substrates in pure organic solvents" Tetrahedron Letters 43 (2002) pp. 8731-8734.
Seis, B., et al. "Kinetics of the Oxygenation of Unsaturated Organics with Singlet Oxygen Generated from $H_2O_2$ by a Heterogeneous Molybdenum Catalyst" J. American Chemical Society (2007) 129 pages 6916-6925.

* cited by examiner

*Primary Examiner* — Paul A Zucker
*Assistant Examiner* — Mark Luderer
(74) *Attorney, Agent, or Firm* — Drinker Biddle & Reath LLP

(57) ABSTRACT

The invention relates to a process for the oxidation of mesitol with singlet oxygen, which is released from hydrogen peroxide, this release taking place in the presence of a bismuth compound as catalyst. In the process, 2,4,6-trimethylquinol is formed in high yield and selectivity as product, which can be used in further reactions for the synthesis of vitamins and in particular of vitamin A and vitamin E.

19 Claims, 4 Drawing Sheets

Fig. 2:

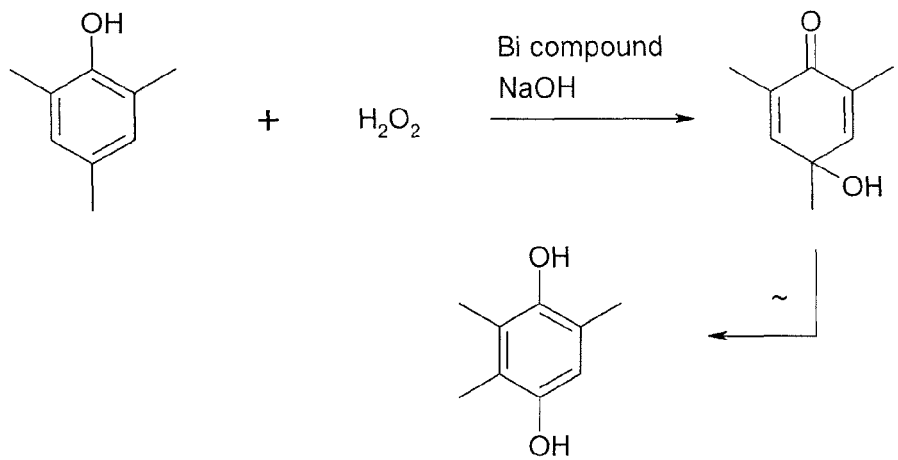

Fig. 3: Catalysts tested:

Example 22 (1) Bi$_2$O$_3$ (CAS NO. 1304-76-3)
Example 23 (2) BiO(NO$_3$) (CAS NO. 10361-46-3)
Example 24 (3) Bi(NO$_3$)$_3$ *5H$_2$O (CAS NO. 10035-06-0)
Example 25 (4) Bismuth subsalicylate: (CAS NO. 14882-18-9)

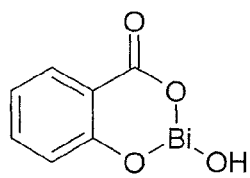

Example 26 (5) Bismuth citrate: (CAS NO. 813-93-4)

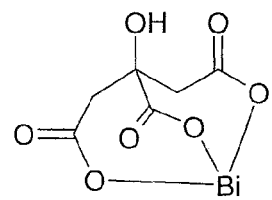

Example 27 (6) Bismuth molybdate (Bi$_2$(MoO$_4$)$_3$) (CAS NO. 13595-85-2)
Example 28 (7) Bi-Co-ZnO Formula (Bi$_2$O$_3$)$_{0.07}$(CoO)$_{0.03}$(ZnO)$_{0.90}$
Example 29 (8) Bismuth subcarbonate (Bi$_2$O$_3$(CO$_3$)) or (BiO)$_2$CO$_3$: (CAS NO 5892-10-4)
Example 30 (9) Bismuth trifluoromethanesulfonate (Bi(SO$_3$CF$_3$)$_3$) (CAS NO. 88189-03-1)

PROCESS FOR THE OXIDATION OF MESITOL

CROSS-REFERENCE TO RELATED APPLICATION

This application claims the benefit of U.S. Provisional Application Ser. No. 61/439,966 filed Feb. 7, 2011, the entire contents of which are incorporated herein by reference in its entirety.

FIELD OF THE INVENTION

The present invention relates to a process for the oxidation of mesitol with singlet oxygen which is released from $H_2O_2$, to a product prepared therefrom, and to the use of said product for producing 2,3,6-trimethylhydroquinone or as a precursor for the synthesis of vitamin E.

BACKGROUND

In recent times, singlet oxygen $^1O_2$ has distinguished itself as oxidizing agent of a variety of double-bond systems. Usually, it is obtained by photochemical routes, by dye molecules, such as for example eosine or methylene blue, excited by electromagnetic radiation giving off their excitation energy to oxygen upon reverting to the ground state and consequently converting it from the triplet state to the singlet state. However, this method of producing singlet oxygen requires the use of strong lights, is therefore expensive and not very suitable for use in large chemical plants.

Another way of producing singlet oxygen is pursued by J.-M. Aubry in Tetrahedron Letters 43 (2002) 8731-8734, in which he releases it from an alkaline $H_2O_2$ solution by means of a molybdenum compound.

However, this procedure is burdened with a number of disadvantages.

For example, in the presence of excessively large amounts of $H_2O_2$, the tetraperoxomolybdate anion is formed from the molybdenum compound used as catalyst and is not able to release singlet oxygen $^1O_2$ from $H_2O_2$. Instead, this requires an oxotriperoxomolybdate, but this is only present in solutions in which $H_2O_2$ is present in a low concentration. However, such low concentrations are only achieved if, during the reaction, only as much $H_2O_2$ is added as disintegrates again through the release of singlet oxygen. Consequently, a very precise dosing of $H_2O_2$ during the reaction is required, involving greater expenditure on apparatus, a slower reaction rate and therefore a low space-time yield. Alternatively, there remains only the option of producing singlet oxygen discontinuously, i.e. in a batch process, and tolerating lower singlet oxygen yields and again longer reaction times.

In order to achieve an adequately high reaction rate, according to Aubry, molybdate ions are to be introduced as catalyst in a concentration of 0.1 mol/l, i.e. in a very large amount (see page 8732, column 1, 1). This increases the manufacturing costs of singlet oxygen $^1O_2$ and of secondary products oxidized with it.

Moreover, according to Aubry, the yield of singlet oxygen $^1O_2$ also depends on the type of counterion which is assigned to the reaction-catalyzing molybdate ion. For example, particularly good yields were achieved with lithium as counterion, but not with potassium (see page 8733, 1st column, 2nd paragraph). However, lithium molybdates are very expensive compounds and therefore make the production of singlet oxygen and thus the oxidation of chemical compounds in general, and of mesitol in particular, more expensive.

In addition, molybdenum compounds in the presence of $H_2O_2$ are only of limited suitability for the reaction with mesitol since the singlet oxygen $^1O_2$ to be produced catalytically for this purpose oxidizes mesitol not only to the quinol, but also to the perquinol, with both compounds being formed in the ratio 1:1 (see table 2). Before further reaction, this perquinol has to firstly be reduced to the quinol, which leads to additional expenditure.

Finally, Aubry was able to establish that the molybdate-catalyzed disproportionation of $H_2O_2$ in the presence of molybdate ions is heavily temperature-dependent and large yields of singlet oxygen $^1O_2$ are obtained at an adequate rate only at elevated temperatures (see page 8733, 2nd column, 2nd paragraph). However, in the case of certain substrates, high temperatures may lead to secondary reactions or else to the thermal decomposition of $H_2O_2$.

In the search for further catalysts for the release of singlet oxygen $^1O_2$, Aubry has identified in J. Am. Chem. Soc. (1985), 107, 5844-5849 the alkaline earth metals Ca, Sr and Ba, elements from groups 3a, 4a, 5a and 6a of the Periodic Table of the Elements, actinides and lanthanides, and also $ClO^-$, $BrO^-$, $Au^+$, $IO_3^-$ and $IO_4^-$. Here, he has detected the singlet oxygen $^1O_2$ through reaction with tetrapotassium rubrene-2,3,8,9-tetracarboxylate by oxidizing said rubrene derivative by the generated singlet oxygen in aqueous-alkaline solution to give the corresponding endoperoxide, and determining its content by spectrometry. For various oxidic compounds of the aforementioned elements of the Periodic Table of the Elements listed in table 1 of this article, yields of endoperoxide of 70% were obtained.

Statements about whether the oxidation of the rubrene derivative with the catalyst for singlet oxygen $^1O_2$ given in table 1 proceeds selectively or led to different compound isomers, however, are not made. It is therefore unclear whether the compounds obtained are pure substances or mixtures. In addition, it is also not specified in what amounts and at what temperatures the catalysts are to be used and/or whether larger amounts of $H_2O_2$ counteract a rapid formation of singlet oxygen $^1O_2$ and thereby reduce the yield of endoperoxide. Finally, it is not discussed whether the compounds identified in table 1 are also suitable for a specific oxidation of mesitol which, on account of its steric shielding, is significantly less accessible to a chemical reaction.

Consequently, for the person skilled in the art, this gives rise to the task of providing a process, which can be used industrially, for producing singlet oxygen $^1O_2$ and secondary products obtained therefrom which no longer has the shortcomings specified above. In particular, the process should be easy to carry out and be cost-effective, produce singlet oxygen $^1O_2$ in a high yield even at high $H_2O_2$ concentrations, and proceed sufficiently rapidly even at room temperature. The provided process should also produce, upon conversion with starting materials, oxidation products as selectively as possible, i.e. with the formation of no or not altogether large amounts of secondary products. Furthermore, it is desired to provide a process with catalysts, the tendency of which to form singlet oxygen $^1O_2$ is only minimally influenced or not influenced at all by counterions. It is also an aim of the invention to arrange individual steps of the inventive process such that a very high yield of singlet oxygen and at the same time a high selectivity with regard to the end product obtained from the prepared singlet oxygen and a starting material is achieved. In particular, it is desired to provide a process with which annular systems such as, inter alia, mesitol can be oxidized regioselectively or largely regioselectively.

Furthermore, the person skilled in the art is presented with the task of providing cost-effective products by means of the process according to the invention, in particular those products which can be used as building blocks for the synthesis of vitamins, in particular of vitamin E.

BRIEF SUMMARY

In a process for the oxidation of mesitol with singlet oxygen, which is released from $H_2O_2$, the invention provides that this release is effected with a bismuth compound as catalyst.

If bismuth compounds are used for the oxidation of mesitol, not only are high product yields achieved, but the formation of a reaction product is clearly preferred over the formation of byproducts, as will be shown below in the examples.

This result is surprising since in the reaction of citronellol with $H_2O_2$ in the presence of a bismuth compound significantly lower conversions, yields and selectivities are achieved, as is likewise shown below in the examples. Consequently, bismuth compounds are only in certain circumstances able to produce high yields of singlet oxygen $^1O_2$ and moreover to effect reaction conditions under which said singlet oxygen $^1O_2$ converts substrate molecules to oxidized species which consist essentially or at least to a large fraction of a single isomer.

Moreover, it is evident from the aforementioned article by Aubry in J. Am. Chem. Soc. (1985), 107, 5844-5849, which deals with the evaluation of various metal oxides, chlorides or nitrates with regard to their ability to release singlet oxygen $^1O_2$, that bismuth compounds are not very suitable in this respect. In table 1 on page 5845, the amount of singlet oxygen formed is, as already mentioned above, quantified by means of spectroscopic determination of a rubrene derivative oxidized by the singlet oxygen. If bismuth in the form of bismuth oxide is used as catalyst, then yields of oxidized rubrene derivative are obtained which are below 10%. When using sodium bismuthate $NaBiO_3$ as catalyst, even virtually no conversion at all, i.e. no oxidation of the specified rubrene derivative induced by singlet oxygen $^1O_2$, was achieved.

BRIEF DESCRIPTION OF THE DRAWINGS

FIG. 2 depicts a reaction scheme for the oxidation of mesitol by the process according to the invention and subsequent rearrangement reaction shown using the example of 2,4,6-trimethylquinol.

FIG. 3 depicts further bismuth compounds which may be used as catalyst.

DETAILED DESCRIPTION OF THE PREFERRED EMBODIMENTS

Figure 1:
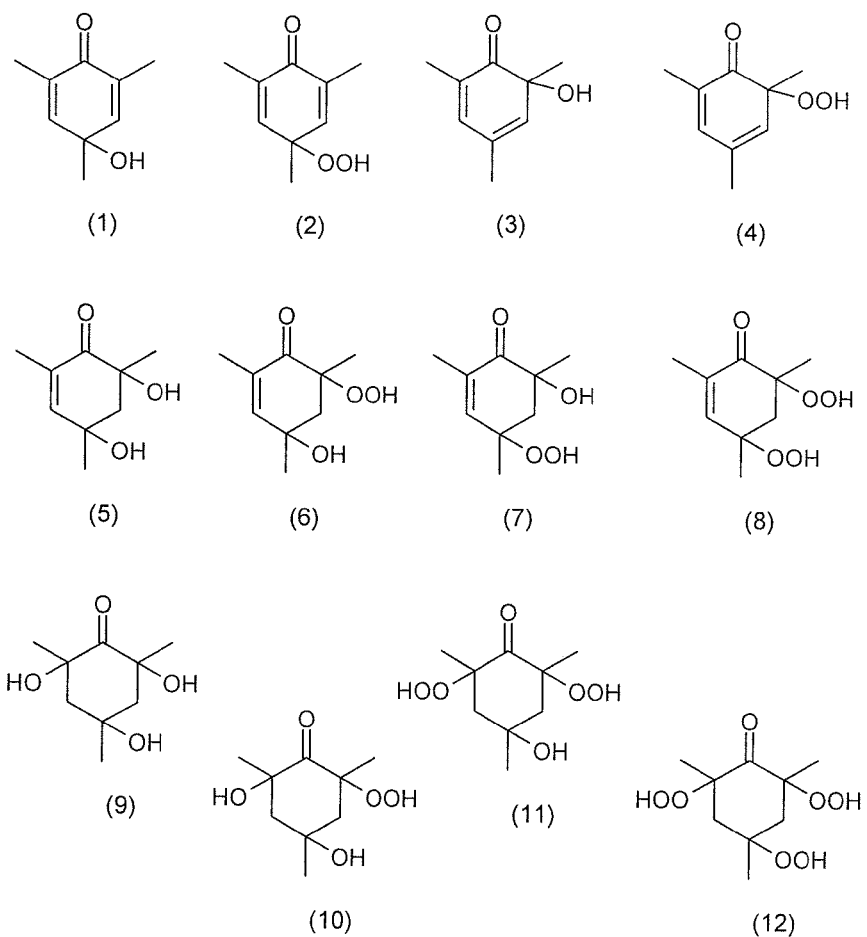
FIG. 1 depicts products obtainable by the inventive process.

It is assumed that mesitol, being an annular system with 3 methyl groups, can be oxidized by singlet oxygen at least with precisely the same difficulty as the aforementioned rubrene derivative and, on account of its severe steric shielding with the 3 methyl groups already mentioned, is probably even less accessible to an oxidation with singlet oxygen $^1O_2$.

Consequently, also against this background, it is surprising that not only can singlet oxygen $^1O_2$ be released in large amounts from $H_2O_2$, but moreover a selective oxidation of mesitol to 2,4,6-trimethylquinol in high yield is achieved by the process according to the invention.

It has also been found that when using a bismuth compound in accordance with the process, the concentration of $H_2O_2$ in the reaction solution has no influence on the formation of singlet oxygen $^1O_2$ and thus on the structure of the catalytically active bismuth compound. In particular, excessively high $H_2O_2$ concentrations do not lead to the formation of highly coordinated bismuth complexes which have lost the ability to release singlet oxygen $^1O_2$ from $H_2O_2$, as is regularly observed with molybdenum oxo compounds.

The term bismuth compound is to be understood as meaning a wide variety of bismuth(III) compounds, which are listed below. The term bismuth compound comprises one or more representatives which are selected from the group bismuth(III) acetate oxide (CAS No. 5142-76-7), basic bismuth (III) carbonate (CAS No. 5892-10-4), which is also referred to as bismuth(III) carbonate oxide or bismuth(III) subcarbonate, bismuth(III) chloride (CAS No. 7787-60-2), bismuth(III) 2-ethylhexanoate or bismuth(III) 2-ethylhexanoic acid (CAS No. 67874-71-9), bismuth(III) nitrate oxide (CAS No. 10361-46-3), basic bismuth(III) nitrate (CAS No. 1304-85-4), which is also referred to as bismuth(III) hydroxide nitrate, bismuth(III) nitrate pentahydrate (CAS No. 10035-06-0), bismuth(III) oxide (CAS No. 1304-76-3), bismuth(III) oxychloride (CAS No. 7787-59-9), bismuth(III) subgallate (CAS No. 99-26-3), bismuth(III) subsalicylate (CAS No. 14882-18-9), bismuth(III) sulfate (CAS No. 7787-68-0), tris(2,2,6,6-tetramethyl-3,5-heptanedionato)bismuth(III) (CAS No. 142617-53-6), bismuth(III) acetate (CAS No. 22306-37-2), bismuth(III) aluminate hydrate (CAS No. 308796-32-9), bismuth lead strontium calcium copper oxide (CAS No. 116739-98-1), bismuth(III) bromide (CAS No. 7787-58-8), bismuth (III) citrate (CAS No. 813-93-4), bismuth(III) fluoride (CAS No. 7787-61-3), bismuth(III) iodide (CAS No. 7787-64-6), bismuth(III) molybdate (CAS No. 13595-85-2), bismuth molybdate (CAS No. 51898-99-8), bismuth molybdenum oxide (CAS No. 13565-96-3), bismuth(III) oxide iodide (CAS No. 7787-63-5), bismuth(III) oxide perchlorate hydrate (CAS No. 66172-93-8), bismuth(III) phosphate (CAS No. 10049-01-1), bismuth(III) selenide (CAS No. 12068-69-8), bismuth strontium calcium copper oxide (CAS No. 114901-61-0), bismuth(III) subnitrate hydrate (CAS No. 13595-83-0), bismuth(III) sulfide (CAS No. 1345-07-9), bismuth(III) telluride (CAS No. 1304-82-1), bismuth(III) titanate (CAS No. 12048-51-0), bismuth(III) tungstate (CAS No. 13595-86-3), bismuth cobalt zinc oxide, Bi—Co—ZnO with the formula $(Bi_2O_3)_{0.07}(CoO)_{0.03}(ZnO)_{0.90}$, bismuth(III) trifluoromethanesulfonate (CAS No. 88189-03-1) and bismuth(III) zirconate (CAS No. 37306-42-6).

A particularly preferred bismuth compound has proven to be one which comprises at least one representative which is selected from the group of bismuth oxides, bismuth nitrates, bismuth nitrate oxides, bismuth cobalt zinc oxide (Bi—Co—Zn—O) with the formula $(Bi_2O_3)_{0.07}(CoO)_{0.03}(ZnO)_{0.90}$, and bismuth(III) citrate since each of these compounds, as is shown below in the examples, in the reaction of mesitol and $H_2O_2$ produces very high yields of 2,4,6-trimethylquinol with high selectivity.

The term mesitol is synonymous with the term 2,4,6-trimethylphenol.

According to the invention, singlet oxygen is to be understood as meaning any type of molecular oxygen in which two unpaired electrons are present, i.e. singlet oxygen comprises both oxygen molecular species in which the two unpaired electrons are present in one and the same π* orbital (term symbol $^1\Delta_g$) and also in two different π* orbitals (term symbol $^1\Sigma^+_g$).

Within the context of the invention, $H_2O_2$ is used in different concentrations which are between 5 and 60% by weight in water depending on the process procedure.

For the rapid and homogeneous process procedure, the process starting material mesitol is introduced as initial charge in a water-miscible solvent.

In a further embodiment of the invention, the starting material mesitol is introduced as initial charge in a mixture of water and water-miscible solvents. The fraction of water in the mixture is between 0.01 and 90% by weight, preferably between 0.02 and 50% by weight and, in a particularly preferred embodiment, between 0.03 and 30% by weight. Particularly in the case of strongly concentrated reaction mixtures, it must be ensured that the content of water is kept rather low since water is formed during the preparation of singlet oxygen $^1O_2$ from $H_2O_2$ However, an excessively high water content leads to the starting material dissolving to a noticeably worse extent, or no longer dissolving at all, in the reaction mixture.

A particularly suitable solvent in which mesitol is introduced as initial charge has proven to be a lower alcohol having 1 to 6 carbon atoms. This alcohol is selected from the group of monohydric, dihydric and/or trihydric alcohols. A particularly preferred trihydric alcohol is selected from the group glycerol, trimethylolpropane or butanetriol. Butanetriol is understood as meaning both 1,2,4-trihydroxybutane and also 1,2,3-trihydroxybutane. Trihydric alcohols, in particular said trihydric alcohols, are well suited because they equally have a polar and nonpolar character and are therefore able to dissolve mesitol very readily, but, on the other hand, they are not so viscous that only a very slow dissolution of the starting material mesitol results.

The dihydric alcohols comprise 1,2-butanediol, 2,3-butanediol, 1,4-butanediol, 1,2-propanediol, 1,3-propanediol, 2,2-dimethyl-1,3-propanediol, 3-methyl-2,4-pentanediol, 1,2-ethanediol, 1,5-pentanediol, 1,2-pentanediol, diethylene glycol (synonymous with β,β'-dihydroxydiethyl ether), triethylene glycol (synonymous with ethylene glycol di-β-hydroxyethyl ether). Moreover, these compounds have the advantage over the trihydric alcohols that in most cases they have a lower viscosity and consequently the reaction mixtures are easier to stir, as a result of which the process can be arranged more cost-effectively.

A lower monohydric alcohol having 1 to 6 carbon atoms comprises one or more representatives from the group comprising methanol, ethanol, 2-propanol, 1-propanol, 2-butanol, 2-methyl-2-butanol, 2-fluorobutanol, 2-methyl-1-propanol, 3-methyl-2-butanol in all isomeric forms, 3-pentanol, 1-butanol, 2-pentanol in all isomeric forms, 3,3-dimethyl-2-butanol, 2,3-dimethyl-2-butanol, 3-methyl-3-pentanol, 2-methyl-2-pentanol, 2-ethoxyethanol synonymous to ethylene glycol monomethyl ether, 2-methyl-3-pentanol, 1-chloro-2-propanol, 2-methyl-1-butanol, 2-chloroethanol, 4-methyl-2-pentanol in all isomeric forms, 3-methyl-1-butanol, 2-chloro-1-propanol in all isomeric forms, 3-methyl-2-pentanol, 2-ethoxyethanol synonymous with ethylene glycol monoethyl ether, 3-hexanol, 2,2-dimethyl-1-butanol, 1-pentanol, 2-hexanol in all isomeric forms, cyclopentanol, 2-isopropoxyethanol synonymous with ethylene glycol monoisopropyl ether, 2,3-dimethyl-1-butanol, 3-methoxy-2-butanol, 1-methoxy-2-propanol, 2-methyl-1-pentanol, 2-ethylbutanol, 2-bromoethanol, 2-n-propoxyethanol, 2,2,2-trichloroethanol, 3-methyl-1-pentanol, 4-methyl-1-pentanol, 1-hexanol, 2-isobutoxyethanol, 2,6-butoxyethanol, 2,4-dimethyl-1-pentanol, 3-chloro-1-propanol, 4-hydroxy-4-methyl-2-pentanol, 2-n-butoxyethanol, 2-aminoethyl alcohol, tetrahydrofuryl alcohol, 3-bromo-1-propanol, 2-methyl-1,2-propanediol, 2,2-dibromoethanol, 2,3-butanediol, 2,3-dichloropropanol, 1,2-propanediol, 2-(2-ethoxy)ethanol synonymous with diethylene glycol monoethyl ether, cyclohexanol, 1-methylcyclopentanol and 2,3-dibromo-1-propanol.

Among these monohydric alcohols, ethanol and methanol have proven to be particularly useful since, on the one hand, they have a low viscosity, and on the other hand the yield of singlet oxygen $^1O_2$ is extremely high and, finally, these two solvents can be mixed, on account of their, as it were, hydrophilic and lipophilic character, directly with many other solvents, which also permits the conversion of starting materials which would not dissolve per se in polar-protic solvents. The use of methanol or ethanol or a mixture thereof as solvent thus increases the rate of the process and makes it more cost-effective because stirring of the reaction mixture is readily possible and the reaction proceeds very quickly.

In a further embodiment of the invention, the solvent comprising mesitol is rendered alkaline using a base. Various bases have been tested and particularly good results with regard to yield and selectivity of 2,4,6-trimethylquinol have been obtained with aqueous or alcoholic solutions of an alkali metal or alkaline earth metal hydroxide. Similarly good results were achieved with an aqueous or alkaline solution of an alcoholate or of a hydride. The different bases can also be used in a mixture with one another and then produce similar results.

Alkali metal or alkaline earth metal hydroxide is understood as meaning all hydroxides which can be prepared with alkali metals of the first group of the periodic table of the elements or alkaline earth metals of the second group of the periodic table of the elements.

Besides the aqueous solutions of alkali metal or alkaline earth metal hydroxides already specified, bases which can be used are also alcoholates or hydrides. Alcoholate is understood as meaning the deprotonated form of at least one of the alcohols listed above which is coordinated with a monovalent, divalent, trivalent or tetravalent metal cation. The alcoholate as such is present either in concentrated form, or else is dissolved in an alcohol, but not in water. A particularly selected alcoholate comprises one or more members which are selected from the group of zinc dialcoholates, of titanium dialcoholates and titanium tetraalcoholates, of alkaline earth metal dialcoholates and of alkali metal alcoholates. Very particularly preferred representatives of an alcoholate are selected from the group comprising lithium isopropylate, sodium methanolate, sodium ethanolate, potassium methanolate, potassium ethanolate, magnesium dimethanolate, magnesium diethanolate, calcium diisopropylate, calcium dimethanolate and calcium diethanolate.

A hydride according to the invention is selected from the group comprising calcium hydride, diisobutyl aluminum hydride, lithium hydride, magnesium hydride, potassium hydride, sodium hydride, titanium(II) hydride or titanium (IV) hydride, triphenyltin hydride and zirconium(II) hydride. On account of their ready availability and their relatively low cost, sodium hydride and/or calcium hydride are particularly preferred. It is also possible to use mixtures of the specified hydrides.

In the course of working for the inventive process, it has also been found that there is a positive effect on its yield if the starting material mesitol is introduced as initial charge in a water-miscible solvent, rendered alkaline with a base and only then reacted with further reactants such as bismuth compound and $H_2O_2$.

If, however, the bismuth compound acting as catalyst in solution is firstly rendered alkaline and only then are mesitol and $H_2O_2$ added as reactants then 2,4,6-trimethylquinol is also formed, but with not quite such high yields as can be seen from example 31.

In one embodiment of the inventive process, the solvent is rendered alkaline using the base, with further reactants only being added after the base has dissolved completely. This development is used particularly when as rapid as possible a process course is not desired, but more likely a high yield of 2,4,6-trimethylquinol. This is achieved only in the event of complete dissolution of base. A further advantage of this embodiment is that, as a consequence of the successive addition of base and further reactants, sudden heating of the reaction mixture, associated with a lower yield of mesitol oxidation product, does not result. However, such a heating is observed if, firstly, upon dissolution or incorporation of base, heat is released and at the same time the formation of singlet oxygen $^1O_2$ in the presence of bismuth compound and $H_2O_2$ likewise proceeds exothermally.

It has also been found that for a high yield of singlet oxygen and consequently of oxidized starting material mesitol, the ratio between the amount of mesitol and the amount of base is decisive. It is important to add the base in a molar ratio which corresponds to the 0.1 to 10-fold molar amount of the mesitol, preferably to the 0.2 to 5-fold molar amount and, in a particularly preferred embodiment, to the 0.5 to 1.5-fold molar amount. Falling below the stated amount of base caused the production of singlet oxygen and thus of end product 2,4,6-trimethylquinol to drop. If amounts larger than those specified above were used, a high yield of singlet oxygen could likewise not be obtained. Consequently, the amount of base based on starting material mesitol is attributed important significance for the invention in accordance with the process. As can be seen below in the examples, particularly high yields of singlet oxygen and therefore of 2,4,6-trimethylquinol are obtained if the base is added in an equimolar or virtually equimolar amount based on mesitol. Virtually equimolar amount means that the molar amounts of mesitol and base differ by not more than 3%.

As has already been stated above, the process according to the invention is preferably carried out at room temperature so as not to adversely affect the product yield as a consequence of possible locally considerable heating. Consequently, one development of the invention provides for achieving an approximately constant reaction temperature by dissolving the base mechanically. "Dissolving mechanically" is understood as meaning the dissolution of the base by means of ultrasound or by means of a stirring mechanism, i.e. without introducing heat.

In one embodiment of the invention, the bismuth compound is added to the mesitol-comprising alkaline solvent. The combination of the process steps—introduction as initial charge of the starting material mesitol in a water-miscible solvent, —rendering alkaline with a base and—subsequent addition of the bismuth compound, increases not only the reaction rate, but also leads to a lower formation of by-products.

Figure 4:
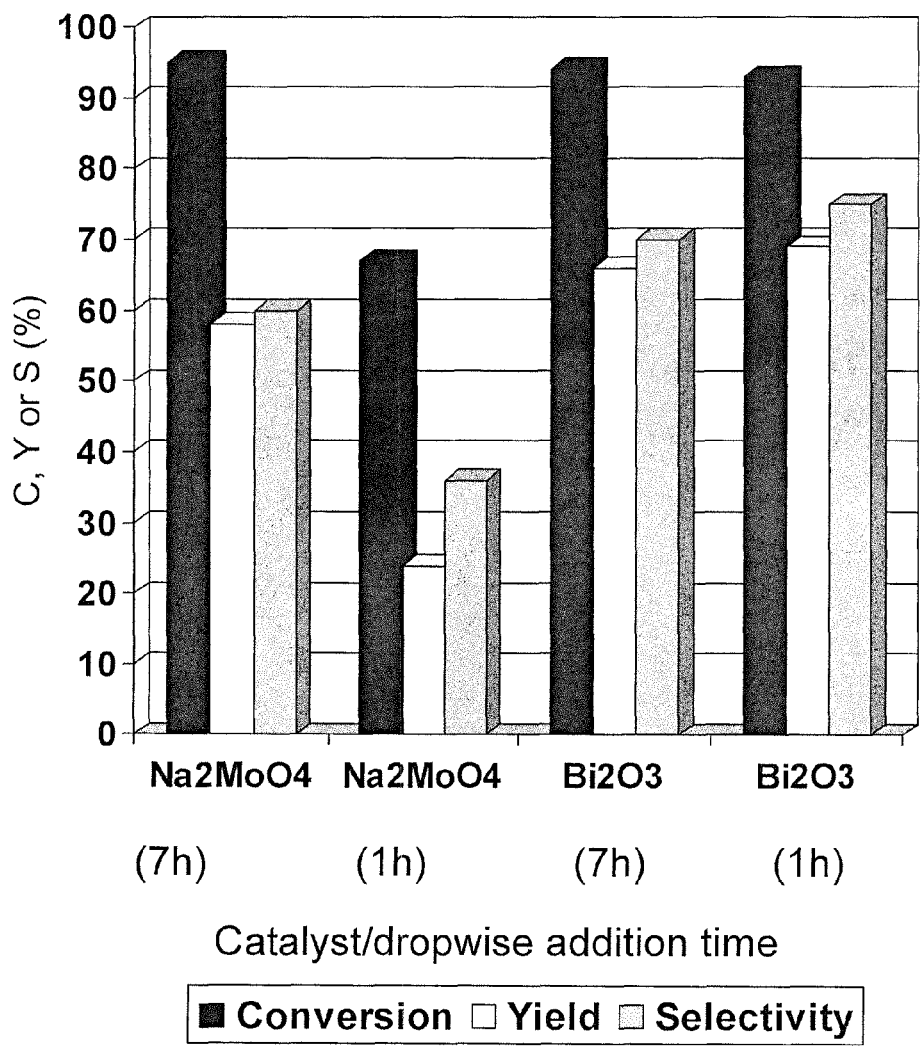
FIG. 4 depicts conversions of mesitol, yields of 2,4,6-trimethylquinol and corresponding selectivities as a function of the reaction time in the presence of the catalyst $Na_2MoO4$ or $Bi_2O_3$.

As can be seen from FIG. 4 (bar diagram), a rapid addition of bismuth compound to the reaction mixture does not lead to a drop in the values for yield and selectivity for the product 2,4,6-trimethylquinol. Consequently, one essential process embodiment consists in adding the bismuth compound to the mesitol-comprising alkaline solvent over a period from 1 min to 10 h, preferably over a period from 2 min to 7 h and, in a particularly favorable variant, over a period from 5 min to 1 h. It is seen that an addition of bismuth compound over 7 h even leads to slightly lower values for yield and selectivity than is the case for an addition over 1 h. Consequently, a quite rapid addition is preferred which, moreover, speeds up the process according to the invention and therefore makes it more cost-effective.

Disodium molybdate $Na_2MoO_4$ as a representative of the molybdo compounds is not able to achieve this since in the case of adding this compound over 1 hour, the values for yield and selectivity of 2,4,6-trimethylquinol drop by about half compared with an addition over 7 hours of disodium molybdate $Na_2MoO4$ to the reaction mixture.

Upon screening the aforementioned bismuth compounds, at least one compound selected from the group of bismuth oxides and/or of bismuth nitrates and/or of bismuth nitrate oxides and/or bismuth cobalt zinc oxide (Bi—Co—Zn—O) and/or bismuth citrate has proven to be particularly suitable for the production of singlet oxygen. During the oxidation of mesitol to 2,4,6-trimethylquinol, all of these compounds produce yields above 40% and selectivities above 50%, as can be seen by reference to examples 22 to 24 (synonymous with examples 5, 11 and 8), 26 and 28.

From this aforementioned group, in turn, that bismuth compound which is selected from the group bismuth(III) oxide ($Bi_2O_3$, CAS No. 1304-76-3), bismuth(III) nitrate pentahydrate ($Bi(NO_3)_3*5H_2O$, CAS No. 10035-06-0), bismuth subnitrate, also to be found under the name bismuth(III) nitrate oxide ($Bi(O)NO_3$, CAS No. 10361-46-3) and bismuth (III) subnitrate monohydrate ($BiO(NO_3)*H_2O$, CAS No. 13595-83-0) or from a mixture of two or more of these compounds, has stood out in particular. When using the aforementioned 4 bismuth compounds, it was likewise possible to obtain yields of mesitol oxidation product above 40%, but this time with a selectivity of $\geq 55\%$.

With regard to selectivity and yield of oxidation product, as can be seen in examples 4 to 6, the bismuth oxides have especially distinguished themselves. Consequently, the bismuth compound in a particularly excellent embodiment of the inventive process is selected from the group of bismuth oxides. In particular, the bismuth compound is bismuth oxide $Bi_2O_3$ (CAS No. 1304-76-3).

A further embodiment of the inventive process determines that the base is added in a molar ratio which corresponds to the 1 to 20.4-fold molar amount of bismuth compound, preferably to the 5 to 15-fold molar amount and, in a particularly preferred embodiment, to the 5 to 10.2-fold molar amount of bismuth compound. Finally, in a highly preferred embodiment, the base is added in a molar amount which corresponds to the 10-fold molar amount of bismuth compound or approximately the 10-fold molar amount. "Approximately the 10-fold molar amount" means that the molar amount of base is 9.8 to 10.2 times greater than that of the bismuth compound.

How the amount of base based on the amount of bismuth compound influences the reaction yield is shown in the experimental examples 16 to 21 by way of example for bismuth oxide ($Bi_2O_3$). However, these results are not limited to bismuth oxide per se, but apply in a similar manner to the other bismuth compounds specified above, in particular to bismuth oxides, bismuth nitrates, bismuth nitrate oxides, bismuth cobalt zinc oxide (Bi—Co—Zn—O) and bismuth citrate. In addition, they are also valid for the last-specified compounds if they are in the form of a mixture or some of them are in the form of a mixture.

A further embodiment of the inventive process is that, per mole equivalent of bismuth compound, between 1 and 50 mole equivalents of mesitol, preferably between 5 and 20 mole equivalents and, in a particularly preferred embodiment, between 5 and 10 mole equivalents, are used.

In many experiments, of which examples 4 to 15 are only a selection, it has been found that, with regard to yield of oxidation product 2,4,6-trimethylquinol and with regard to the selectivity of the reaction, between 1 and 50 mole equivalents of mesitol should be reacted per mole equivalent of bismuth compound. Satisfactory yields were achieved when between 5 and 20 mole equivalents of mesitol were used per mole equivalent of catalytically active bismuth compound. Finally, the highest yields of oxidized mesitol were achieved at a molar ratio between bismuth compound and mesitol of 1:10 to 1:20, with a 10-fold molar excess of mesitol per mole equivalent of bismuth compound clearly producing the best results. Accordingly, in one particularly productive embodiment of the invention, 10 mole equivalents of mesitol are used per mole equivalent of bismuth compound.

A further embodiment of the inventive process envisages that $H_2O_2$ is added to the alkaline solution comprising mesitol and bismuth compound.

According to the invention, it is beneficial for the process procedure if the starting material mesitol, the bismuth compound and the alkaline solvent are already present before hydrogen peroxide ($H_2O_2$) is added.

If this procedure is not adopted, but instead a solvent rendered alkaline is admixed with a mixture of hydrogen peroxide and mesitol, then the yields of product 2,4,6-trimethylquinol obtained are not as high as can be seen in example 31.

As has already been established above, the addition of base is essential to the functioning of the inventive process. In particular, it can be seen in examples 16 to 21 that, in the absence of base, both the conversion of mesitol, and also the yield of 2,4,6-trimethylquinol and also the selectivity with which it is obtained decrease considerably. It is assumed that said base has a catalytic effect, probably by deprotonating at least one of the compounds of starting material, bismuth compound and/or $H_2O_2$ and thus making it more readily accessible and/or more reactive. Accordingly, the ratio of base: $H_2O_2$ is also attributed inventive significance. In a further embodiment of the process, the invention envisages therefore that the molar ratio between base and $H_2O_2$ is between 1:4 and 1:20, preferably between 1:8 and 1:15 and, in a particularly preferred embodiment, between 1:9 and 1:12. Particularly good yields and selectivities can be found in examples 4 to 15. Consequently, a highly preferred embodiment of the inventive process envisages that the molar ratio between base and $H_2O_2$ is between 1:9.8 and 1:10.

In a further embodiment, the process according to the invention is characterized in that per mole equivalent of mesitol, a 2 to 70-fold molar excess, preferably a 5 to 40-fold and, in a particularly favorable embodiment, a 10 to 30-fold molar excess of $H_2O_2$ is added to the alkaline solvent.

A cost-determining factor for the reaction procedure is the amount of starting material, in the present case mesitol. Consequently, it is desired to react this as far as is practicable with the singlet oxygen $^1O_2$ generated from $H_2O_2$ to give the corresponding 2,4,6-trimethylquinol. Consequently, an excess of hydrogen peroxide is used. However, for reasons of cost, on the other hand as well, it is again important not to make this $H_2O_2$ excess too great. Consequently, based on mesitol, a 10 to 30-fold molar excess of $H_2O_2$ has proven particularly useful. It is evident from examples 4 to 15 that, per mole equivalent of mesitol, a 10-fold molar excess of $H_2O_2$ is particularly preferably added to the alkaline solvent.

Surprisingly, it has moreover been found that the yield of singlet oxygen $^1O_2$ is virtually independent of the concentration of the hydrogen peroxide used (see in this regard examples 4 to 15). For reasons of cost, the hydrogen peroxide $H_2O_2$ used according to the invention has a concentration of from 5 to 60 wt %, preferably from 10 to 55 wt % and, in a particularly preferred embodiment, from 30 to 50 wt % in water. 30 to 50% strength hydrogen peroxide solutions are available on the market at favorable cost and can be stored and processed without problems, and are thus consequently preferably used.

In contrast to bismuth compounds, in particular molybdate species react sensitively to the concentration and amount of $H_2O_2$ used. As already mentioned above, if the $H_2O_2$ is too highly concentrated or if $H_2O_2$ is added too quickly to a reaction medium admixed with catalyst compound, they can lose their ability to release singlet oxygen $^1O_2$.

In a further variant of the inventive process, $H_2O_2$ is added to the alkaline solvent comprising mesitol and bismuth compound in one batch.

By adding $H_2O_2$ in one batch, the process procedure can be made shorter and does not need an addition control system for $H_2O_2$. Consequently, this embodiment of the invention is particularly cost-effective and can be used particularly if small amounts of mesitol are to be reacted.

A further variant of the process according to the invention envisages that the $H_2O_2$ is added to the alkaline solvent comprising mesitol and bismuth compounds over a period of from 30 min to 14 h, preferably from 45 min to 7 h and particularly preferably over a timespan from 1 h to 7 h.

Depending on the amount of mesitol starting material, the use of the corresponding amount of $H_2O_2$ leads to local heat phenomena in the reaction mixture. These are observed particularly in the case of large amounts of mesitol, which require corresponding amounts of $H_2O_2$, and when using a 50% strength by weight $H_2O_2$ solution. Said local heating promotes the formation of by-products and reduces the values for yield and selectivity. This disadvantage can be overcome by adding $H_2O_2$ within the timeframe stated above and, in a particularly advantageous manner, over a timespan from 1 h to 7 h.

If large amounts of mesitol as starting material and a 50% strength by weight $H_2O_2$ solution are used, then for the reasons specified above, in a highly preferred variant of the process according to the invention, it is appropriate for the $H_2O_2$ to be added to the alkaline solvent comprising mesitol and bismuth compound over a period of from 2 h to 7 h.

Local heating of the reaction mixture, which requires a continuous addition of $H_2O_2$ over a prolonged period, was not observed with relatively small amounts of mesitol starting material and particularly when using $H_2O_2$ solutions with a 30% strength by weight fraction of $H_2O_2$.

As already stated above, the concentration of $H_2O_2$ does not influence the ability of the bismuth compound to release singlet oxygen $^1O_2$ from $H_2O_2$ and consequently to shift the formation of 2,4,6-trimethylquinol to smaller values. This is true to a particularly notable extent for the bismuth compounds bismuth oxide $Bi_2O_3$ (CAS No. 1304-76-3, see examples 5 and 13) and for bismuth nitrate pentahydrate $Bi(NO_3)_3*5H_2O$ (CAS No. 10035-06-0, see examples 8 and 14).

Consequently, a further embodiment of the invention envisages that the $H_2O_2$ is added to the alkaline solvent continuously, associated with a time- and cost-saving execution of the process according to the invention.

In contrast to molybdo compounds, which are able to release increasingly larger fractions of singlet oxygen $^1O_2$ from hydrogen peroxide solution as the temperature increases (see Tetrahedron Letters 43 (2002) 8731-8734, page 8731, right-hand column, paragraph 2), bismuth compounds according to the invention are able to generate uniform amounts of singlet oxygen $^1O_2$ from $H_2O_2$ irrespective of the temperature. Consequently, the process according to the invention envisages a further embodiment, that the $H_2O_2$ is added at a temperature of the solvent of 0-90° C., preferably 5-50° C. and particularly preferably 10-30° C. Consequently, it is also possible to carry out the reaction at room temperature, which is thus cost-effective and nevertheless not time-consuming.

Cost-efficient operation of the process according to the invention is also helped by keeping the fraction of catalytically active bismuth compound based on the amount of $H_2O_2$ very low and nevertheless obtaining a high yield of product, in particular 2,4,6-trimethylquinol. Consequently, a further inventive embodiment envisages that the molar ratio between bismuth compound and $H_2O_2$ is between 1:20 and 1:400, preferably between 1:50 and 1:205 and particularly preferably between 1:50 and 1:105. Exceptionally high values for the yield and the selective generation of 2,4,6-trimethylquinol are achieved if the molar ratio between bismuth compound and $H_2O_2$ is between 1:100 and 1:100.7.

Within the context of this application, yield in % means the number of moles of product 2,4,6-trimethylquinol which are obtained, divided by the amount of mesitol used, likewise expressed in moles, times 100.

Within the context of this disclosure, the weight percentage is referred to as wt % or % by weight, the two terms being used synonymously.

Within the context of this application, selectivity in % is understood as meaning the number of moles of product 2,4,6-trimethylquinol divided by the converted amount of mesitol, likewise expressed in moles, times 100.

A preferred execution of the process according to the invention is attained when a high selectivity is achieved since then exclusively or virtually exclusively unreacted mesitol can be recovered and obviously re-used. Because separating off the product 2,4,6-trimethylquinol from unreacted mesitol is associated with a certain expenditure, a particularly preferred procedure of the process according to the invention is then in particular present when a high yield is achieved, thus when a high selectivity of 2,4,6-trimethylquinol coupled with a simultaneously high conversion of mesitol is attained.

The invention further provides a product which is obtainable from the process described above. Product is understood as meaning at least one of the compounds 2,4,6-trimethylquin-4-ol (1), 2,4,6-trimethyl-4-perquinol (2), 2,4,6-trimethylquin-2-ol (3), 2,4,6-trimethyl-2-perquinol (4), 2,4,6-trimethylquin-2,4-diol (5), 2,4,6-trimethyl-2-hydroperoxyquin-4-ol (6), 2,4,6-trimethyl-4-hydroperoxyquin-2-ol (7), 2,4,6-trimethyl-2,4-dihydroperoxyquinol (8), 2,4,6-trimethylquin-2,4,6-triol (9), 2,4,6-trimethyl-6-perhydroxyquin-2,4-diol (10), 2,4,6-trimethyl-2,6-diperhydroxyquin-4-ol (11) and 2,4,6-trimethyl-2,4,6-trihydroperoxyquinol (12), as depicted in FIG. 1, and mixtures thereof.

Very particular preference is given to the product 2,4,6-trimethylquin-4-ol since it is formed in large amounts according to the process and represents a key compound for the synthesis of further natural substances.

A further developed embodiment of the invention envisages the use of the resulting product for producing 2,3,6-trimethylhydroquinone. Said molecule is obtained by heating 2,4,6-trimethylquinol under nonacidic conditions in a liquid medium at a temperature of at least 110° C. such that the pH does not drop below 6. This medium preferably includes a basic compound which comprises an alkali metal and/or alkaline earth metal.

Furthermore, the invention envisages the use of the product prepared in the process according to the invention as precursor for the synthesis of vitamin E. This use is of great technical benefit insofar as it renders superfluous the oxidation, regularly used for this purpose, of the precursor 2,3,6-trimethylphenol, with the very corrosive catalyst system based on copper(II) chloride. Moreover, mesitol is significantly more cost-effective to obtain than said 2,3,6-trimethylphenol.

Further features, details and advantages of the invention arise from the wording of the claims and also from the following description of examples with reference to the tables and figures.

These show:

FIG. 1: Products obtainable by the inventive process

FIG. 2: Reaction scheme for the oxidation of mesitol by the process according to the invention and subsequent rearrangement reaction shown using the example of 2,4,6-trimethylquinol.

FIG. 3: Further bismuth compounds used as catalyst.

FIG. 4: Conversions of mesitol, yields of 2,4,6-trimethylquinol and corresponding selectivities as a function of the reaction time in the presence of the catalyst $Na_2MoO_4$ or $Bi_2O_3$.

Figure 5:
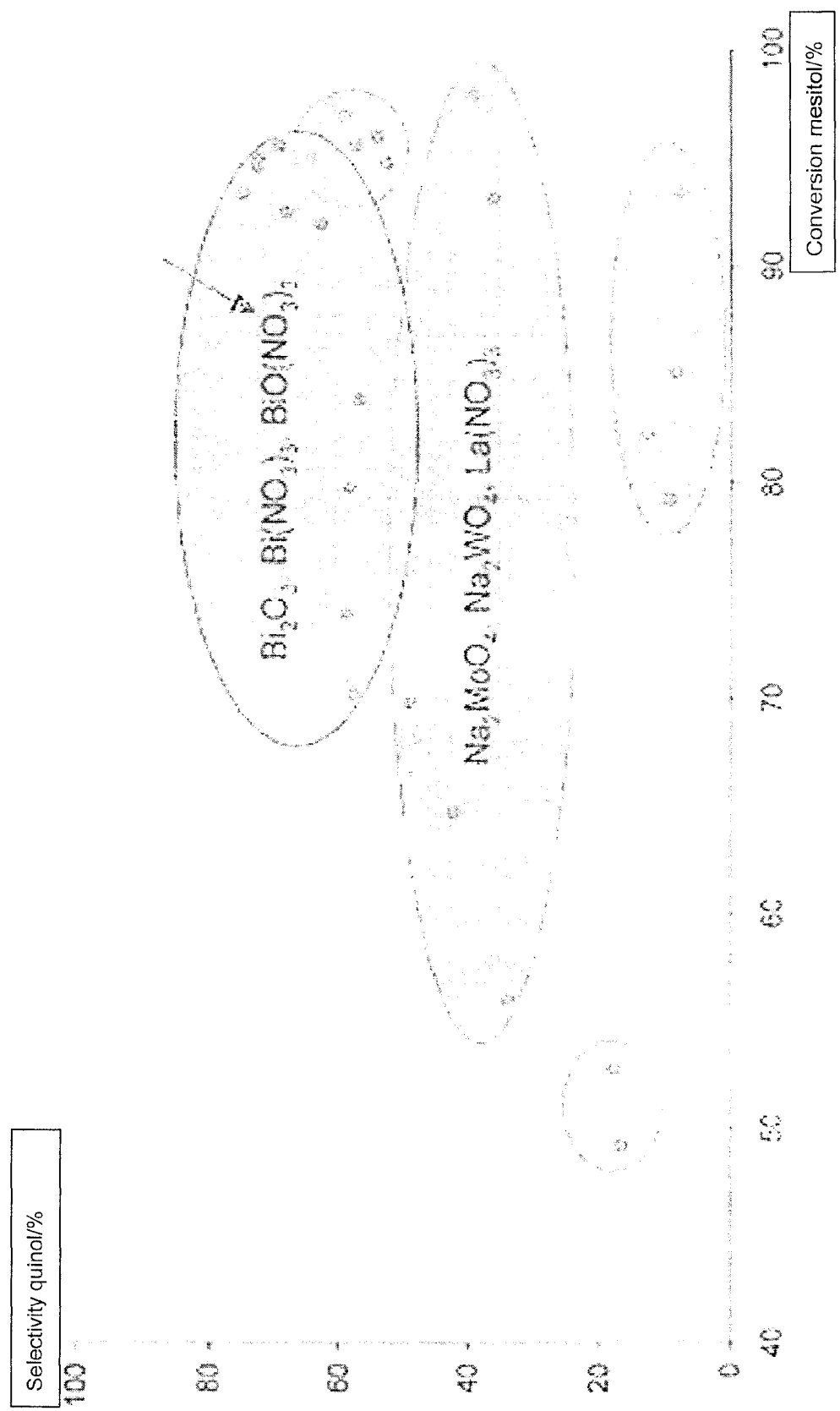
FIG. 5 depicts a functional plot of the selectivity for obtaining 2,4,6-trimethylquinol in % as a function of the conversion of mesitol in %.

FIG. 5: Functional plot of the selectivity for obtaining 2,4,6-trimethylquinol in % as a function of the conversion of mesitol in %.

Tab. 1: Oxidation of various unsaturated starting materials with bismuth compound and $H_2O_2$ in a basic environment, and also conversions, yields and selectivity values.

Tab. 2: Oxidation of mesitol in the presence of $H_2O_2$ and bismuth oxide $Bi_2O_3$ as a function of the added amount of base, and also conversions, yields and selectivities.

Tab. 3: Conversion of mesitol, and also yields of quinol and associated selectivities when using the bismuth compounds specified in FIG. 3.

FIG. 2 shows the reaction scheme for the reaction of mesitol with $H_2O_2$ in the presence of a base, and of a bismuth compound as catalyst to give the product 2,4,6-trimethylquinol (1). The last-mentioned compound can be rearranged under nonacidic conditions at a temperature of at least 110° C. to give 2,3,6-trimethylhydroquinone if the pH does not drop below 6 during the reaction. This is preferably achieved by adding to the reaction mixture a basic compound which comprises either an alkali metal or an alkaline earth metal or a mixture of compounds of both metals. It is essential for achieving high conversions of mesitol, high yields of 2,4,6-trimethylquinol and high selectivities with regard to this compound, to add the starting materials together in a specific manner. Moreover, it is of importance for how long the catalytically active bismuth compound is brought into contact with the other starting materials. In a typical example for carrying out the process, the procedure is as follows:

5.00 g (36.7 mmol) of mesitol are introduced as initial charge in 60 ml of methanol and admixed with 1.5 g (37.5 mmol) of NaOH. In one process procedure aimed not at time but at very high yields, the resulting suspension is stirred until the sodium hydroxide (NaOH) has dissolved completely (ca. 10 min). If a rapid reaction procedure is what is important and it is of little importance if the yield of 2,4,6-trimethylquinol turns out somewhat lower, then complete dissolution of the sodium hydroxide can be omitted. However, it must be ensured that the starting material mesitol is introduced as initial charge in a water-miscible solvent, rendered alkaline using a base and only then reacted with further reactants such as, for example, bismuth compound and $H_2O_2$, in order to ensure that the yield of 2,4,6-trimethylquinol and the selectivity with which this yield is achieved do not drop severely. Following complete addition of the sodium hydroxide (NaOH) or following complete dissolution of the sodium hydroxide (NaOH), the reaction mixture obtained in this way is admixed with 0.05 to 0.20 mole equivalents of bismuth compound as catalyst. The reaction mixture is kept at room temperature throughout the entire time or at the reaction temperature. Care is taken, both during the addition of NaOH and also during the addition of catalyst, to achieve a dissolution of base, in particular NaOH, solely by means of stirring in order to avoid too great a temperature increase. 25.0 g (corresponding to 367.7 mmol) of $H_2O_2$ with a concentration of 50% by weight in water are then metered in over the course of 2 to 7 h at room temperature. The pale yellow suspension is then stirred for a further 12 hours at room temperature. When this time has elapsed, the reaction mixture is analyzed by means of quantitative gas chromatography using an internal standard. Oxidation reactions carried out in accordance with this process protocol, and the values obtained for conversion of mesitol, yield of 2,4,6-trimethylquinol and the associated selectivity of the reaction are listed in examples 4 to 12 of table 1.

It is seen that the best yields and selectivities with regard to the product 2,4,6-trimethylquinol are obtained with bismuth oxide (CAS No. 1304-76-3) as catalytically active compound. In addition, under basic conditions, increased yields are achieved at a molar ratio of bismuth compound to mesitol to $H_2O_2$ of 1:10:100. Here, it is moreover evident that it is likewise beneficial for the process result if base and mesitol are used in equimolar or approximately equimolar amounts. This also applies if a 10-fold excess of $H_2O_2$ based on the starting material mesitol is used.

In examples 13 to 15, which are for the greatest part in agreement with examples 4, 8 and 11, instead of a 50% strength by weight $H_2O_2$ solution, one with only a 30% strength by weight content of $H_2O_2$ is used. Here too, the best yields and selectivities are achieved with bismuth(III) oxide (CAS No. 1304-76-3) as in example 5. Consequently, the concentration of $H_2O_2$ in the $H_2O_2$ solution used only has a slight influence on the yield of 2,4,6-trimethylquinol (1), synonymous with 2,4,6-trimethylquin-4-ol (1). The latter is sometimes slightly increased when using 30% strength by weight $H_2O_2$ compared with 50% strength by weight $H_2O_2$.

As already mentioned above, the addition of base has an influence on the amount of converted mesitol, on the yield of 2,4,6-trimethylquinol as an inventive product and on the selectivity with regard to this compound. Using the example

TABLE 1

| | β-Citronellol | | | Bismuth compound | | | NaOH | | | H2O2 | | | Conversion Citronellol % | Yield Diols % | Selectivity Diols % |
|---|---|---|---|---|---|---|---|---|---|---|---|---|---|---|---|
| | [g] | [mmol] | eq. | [g] | [mmol] | eq. | [ml] | [mol/l] | eq. | [g] | [mmol] | eq. | | | |
| | | | | $Bi(NO_3)_3*5H_2O$ (1) | | | | | | (4) | | | | | |
| Example 1 | 4.07 | 25 | 33.3 | 0.296 | 0.75 | 1 | 0.45 | 5 | 3 | 22.1 | 325 | 433 | 28 | 12 | 41 |
| Example 2 | 4.07 | 25 | 33.3 | 0.296 | 0.75 | 1 | 0.45 | 5 | 3 | 22.1 | 325 | 433 | 33 | 15 | 45 |
| | | | | $Bi_2O_3$ (2) | | | | | | | | | | | |
| Example 3 | 4.07 | 25 | 33.3 | 0.35 | 0.75 | 1 | 0.45 | 5 | 3 | 22.1 | 325 | 433 | 17 | 4 | 25 |

| | Mesitol | | | Bismuth compound | | | NaOH | | | H2O2 | | | Conversion Mesitol % | Yield Quinol % | Selectivity Quinol % |
|---|---|---|---|---|---|---|---|---|---|---|---|---|---|---|---|
| | [g] | [mmol] | eq. | [g] | [mmol] | eq. | [g] | [mmol] | eq. | [g] | [mmol] | eq. | | | |
| | | | | $Bi_2O_3$ (2) | | | | | | (4) | | | | | |
| Example 4 | 5.00 | 36.7 | 20 | 0.86 | 1.835 | 1 | 1.5 | 37.5 | 20.4 | 25.0 | 367.7 | 200 | 93 | 63 | 68 |
| Example 5 | 5.00 | 36.7 | 10 | 1.71 | 3.67 | 1 | 1.5 | 37.5 | 10.2 | 25.0 | 367.7 | 100 | 95 | 68 | 72 |
| Example 6 | 5.00 | 36.7 | 5 | 3.42 | 7.34 | 1 | 1.5 | 37.5 | 5.1 | 25.0 | 367.7 | 50 | 89 | 52 | 58 |
| | | | | $Bi(NO_3)_3 \cdot *5H_2O$ (1) | | | | | | | | | | | |
| Example 7 | 5.00 | 36.7 | 20 | 0.73 | 1.835 | 1 | 1.5 | 37.5 | 20.4 | 25.0 | 367.7 | 200 | 74 | 34 | 59 |
| Example 8 | 5.00 | 36.7 | 10 | 1.45 | 3.67 | 1 | 1.5 | 37.5 | 10.2 | 25.0 | 367.7 | 100 | 80 | 44 | 55 |
| Example 9 | 5.00 | 36.7 | 5 | 2.90 | 7.34 | 1 | 1.5 | 37.5 | 5.1 | 25.0 | 367.7 | 50 | 67 | 35 | 53 |
| | | | | $BiO(NO_3)$ (3) | | | | | | | | | | | |
| Example 10 | 5.00 | 36.7 | 20 | 0.53 | 1.835 | 1 | 1.5 | 37.5 | 20.4 | 25.0 | 367.7 | 200 | 70 | 40 | 58 |
| Example 11 | 5.00 | 36.7 | 10 | 1.05 | 3.67 | 1 | 1.5 | 37.5 | 10.2 | 25.0 | 367.7 | 100 | 77 | 52 | 68 |
| Example 12 | 5.00 | 36.7 | 5 | 2.11 | 7.34 | 1 | 1.5 | 37.5 | 5.1 | 25.0 | 367.7 | 50 | 83 | 51 | 61 |
| | | | | $Bi_2O_3$ (2) | | | | | | (5) | | | | | |
| Example 13 | 2.50 | 18.4 | 10 | 0.86 | 1.84 | 1 | 0.75 | 18.8 | 10.2 | 21.0 | 185.3 | 100 | 93 | 70 | 75 |
| | | | | $Bi(NO_3)_3*5H_2O$ (1) | | | | | | | | | | | |
| Example 14 | 2.50 | 18.4 | 10 | 0.73 | 1.84 | 1 | 0.75 | 18.8 | 10.2 | 21.0 | 185.3 | 100 | 83 | 48 | 57 |
| | | | | $BiO(NO_3)$ (3) | | | | | | | | | | | |
| Example 15 | 2.50 | 18.4 | 10 | 0.53 | 1.84 | 1 | 0.75 | 18.8 | 10.2 | 21.0 | 185.3 | 100 | 80 | 47 | 58 | eq. = Mole equivalents based on the amount of Bi compound used
(1): MW = 394.7 g/mol,
(2): MW = 466.7 g/mol,
(3): MW = 286.98 g/mol,
(4): MW = 34.01 g/mol, 50 wt % solution in water,
(5): MW = 34.01 g/mol, 30 wt % solution in water of the base sodium hydroxide (NaOH), this influence was investigated and documented in table 2 below.

In detail, 5 g (36.7 mmol) of mesitol are introduced as initial charge in 60 ml of methanol and this solution is admixed with different amounts of sodium hydroxide (NaOH), with from 0 to 2 mole equivalents of NaOH being added in different experiments, based on the amount of mesitol used. The resulting suspension is stirred until the sodium hydroxide (NaOH) has completely dissolved (ca. 10 min). It is then admixed with 1.71 g (3.67 mmol corresponding to 0.1 mole equivalents based on the amount of mesitol used) of bismuth oxide $Bi_2O_3$ (CAS No. 1304-76-3) and, afterwards, 25.0 g (367.7 mmol corresponding to 10 mole equivalents based on the amount of mesitol used) of $H_2O_2$ in the form of a 50% strength by weight aqueous solution are added over a period of 7 h at room temperature. The pale yellow suspension is then stirred for a further 12 h at room temperature and, after this time has elapsed, the reaction mixture is analyzed by means of gas chromatography.

TABLE 2

Variation in the amount of base:

| Example* | Catalyst | Equiv. NaOH | $C_{mesitol}$ | $Y_{quinol}$ | $S_{quinol}$ |
|---|---|---|---|---|---|
| 16 | $Bi_2O_3$ | 0.0 | 7.8% | 1.8% | 23% |
| 17 | $Bi_2O_3$ | 0.1 | 40% | 24% | 61% |
| 18 | $Bi_2O_3$ | 0.5 | 92% | 55% | 60% |
| 19 | $Bi_2O_3$ | 1.0 | 95% | 68% | 72% |
| 20 | $Bi_2O_3$ | 1.5 | 79% | 28% | 36% |
| 21 | $Bi_2O_3$ | 2.0 | 73% | 25% | 34% |

*all examples in MeOH with - based on mesitol - 0.1 equiv. $Bi_2O_3$, 10 equiv. $H_2O_2$ (50% by weight in $H_2O$) added dropwise over 7 h.

It is seen from tab. 2 above that in the absence of base (NaOH), the conversion of mesitol at 7.8%, and the yield of 2,4,6-trimethylquinol at 1.8% and a selectivity achieved in this respect of 23% lags significantly behind the minimum values demanded for an industrial process. If 0.1 to 10 mole equivalents and in particular 0.1 to 2 mole equivalents of base, based on the amount of mesitol used, are present in the reaction mixture, then the yields already range from 24 to 68% of 2,4,6-trimethylquinol, with selectivities of from 34 to 72% being achieved. Consequently, one embodiment of the inventive process envisages that the base is added in a molar ratio which corresponds to the 0.1 to 2-fold molar amount of the mesitol. Although this embodiment is inferred from the examples and relates to $Bi_2O_3$ (CAS No. 1304-76-3), it is, however, not limited to this bismuth compound, but a concrete part of the invention and can thus be used directly in the general description with the aforementioned bismuth compounds and optionally as subject matter for an inventive claim.

Furthermore, it is evident from tab. 2 that when adding from 0.5 to 1.5 mole equivalents of NaOH per equivalent of mesitol and in particular at 0.5 to 1 mole equivalent of NaOH per equivalent of mesitol, conversions of 79% and more of mesitol, yields of 2,4,6-trimethylquinol up to 68% and selectivities of 36% and more are achieved. If 0.5 to 1 mole equivalent of NaOH are used per mole equivalent of mesitol, even 92% and more of mesitol are converted, yields of 2,4,6-trimethylquinol from 55 to 68% are obtained and this with a selectivity of from 60 to 72%. Consequently, a further inventive embodiment envisages that the base is added in a molar ratio, which corresponds to the 0.5 to 1-fold molar amount of the mesitol. This embodiment also is not limited to the examples, but can also be realized with other bismuth compounds as stated above, is a concrete part of the invention and can thus be used directly in the general description and optionally as subject matter for an inventive claim.

Besides the compounds bismuth oxide ($Bi_2O_3$, CAS No. 1304-76-3), bismuth(III) nitrate pentahydrate ($Bi(NO_3)_3 \cdot H_2O$, CAS No. 10035-06-0) and bismuth(III) oxide nitrate ($BiO(NO_3) \cdot H_2O$, CAS No. 13595-83-0) specified in tab. 1, further bismuth compounds were investigated as regards their ability to oxidize mesitol by means of singlet oxygen $^1O_2$ released from $H_2O_2$ to give 2,4,6-trimethylquinol (1). These compounds are depicted together with those specified above in FIG. 3 and were reacted in accordance with the following process procedure.

For examples 22 to 30, 5.00 g (36.7 mmol, 1 mole equivalent) of mesitol are introduced as initial charge in 60 ml of methanol and admixed with 1.50 g (37.5 mmol) of sodium hydroxide (NaOH). The resulting suspension is stirred until the sodium hydroxide (NaOH) has completely dissolved, which requires about 10 min. The reaction mixture is then admixed with 0.1 mole equivalent (or 0.05 in example 28b) of one of the bismuth compounds specified in examples 22 to 30, where 0.1 mole equivalent refers to the amount of mesitol used. Afterwards, 25.0 g (367.7 mmol) of $H_2O_2$ as 50% strength by weight solution in water are metered in over a period of 7 h at room temperature. The pale yellow suspension is then stirred for a further 12 h at room temperature and the reaction mixture then obtained is analyzed by means of gas chromatography. The results obtained can be found in tab. 3.

TABLE 3

| Experiment* | Example | Catalyst | Equiv. Catalyst | $C_{mesitol}$ | $Y_{quinol}$ | $S_{quinol}$ |
|---|---|---|---|---|---|---|
| VS 08-019 | 22 | $Bi_2O_3$ | 0.10 | 95% | 68% | 72% |
| VS 08-021 | 23 | $BiO(NO_3)$ | 0.10 | 77% | 52% | 68% |
| VS 08-012 B | 24 | $Bi(NO_3)_3 \cdot 5H_2O$ | 0.10 | 80% | 44% | 55% |
| DA 1511-1 | 25 | Bismuth(III) subsalicylate | 0.10 | 74% | 20% | 27% |
| DA 1511-2 | 26 | Bismuth(III) citrate | 0.10 | 82% | 44% | 53% |
| DA 1511-3 | 27 | (6) | 0.10 | 84% | 29% | 34% |
| DA 1513-1 | 28 | (7) | 0.10 | 94% | 51% | 54% |
| DA 1514 | 28b | (7) | 0.05 | 91% | 45% | 50% |
| DA 1513-2 | 29 | (8) | 0.10 | 89% | 41% | 46% |
| DA 1513-3 | 30 | (9) | 0.10 | 81% | 26% | 32% |

Tab. 3 reveals that, besides the already investigated compounds bismuth oxide (CAS No. 1304-76-3), bismuth subnitrate and also bismuth(III) oxide nitrate ($BiO(NO_3)$, CAS No. 10361-46-3) and bismuth(III) nitrate pentahydrate ($Bi(NO_3)_3 \cdot 5H_2O$, CAS No. 10035-06-0), also the compounds bismuth(III) citrate (CAS No. 813-93-4) and bismuth cobalt zinc oxide (Bi—Co—Zn—O) with the formula $(Bi_2O_3)_{0.07}(CoO)_{0.03}(ZnO)_{0.90}$ produce conversions of mesitol above 80%, yields greater than 44% and selectivities ≥53%.

Bismuth compounds are therefore also preferred as catalyst for the oxidation of mesitol by means of singlet oxygen $^1O_2$ released from $H_2O_2$ because they produce larger amounts of the product 2,4,6-trimethylquinol within shorter times, as can be seen from FIG. 4. This surprising effect ensures that the process according to the invention can be carried out significantly more quickly than a comparable process in which molybdates are used as catalyst.

To obtain the results in FIG. 4, mixtures with bismuth oxide were prepared as in example 5, although the bismuth compound was added in one case over a period of 7 h and in a further experiment over a period of 1 h. The same experiment was carried out again but using sodium molybdate ($Na_2MoO_4$) as catalytically active compound instead of the bismuth compound.

It is seen that with bismuth oxide as catalyst the yield of 2,4,6-trimethylquinol and the selectivity with which this compound is obtained is increased compared with using the molybdate catalyst. Moreover, it is notable that when using sodium molybdate ($Na_2MoO_4$) yield and selectivity increase if the addition of molybdate compound takes place over a period of 7 h instead of 1 h.

For bismuth compounds and in particular for bismuth oxide ($Bi_2O_3$, CAS No. 1304-76-3), by contrast, a result reciprocal of the behavior is obtained, i.e. when adding the bismuth compound and in particular bismuth oxide ($Bi_2O_3$) over a period of 1 h, higher yields of 2,4,6-trimethylquinol and moreover a higher selectivity based on all oxidation products are achieved than when adding said bismuth compound over a period of 7 h.

If bismuth compounds and in particular bismuth oxide ($Bi_2O_3$) are added as catalyst to the reaction mixture over a period of 1 h, then the yield of 2,4,6-trimethylquinol is 70% and the selectivity with regard to this compound is 75%. However, if the addition of bismuth oxide ($Bi_2O_3$) takes place over a period of 7 h, a yield of 2,4,6-trimethylquinol of 66% with a selectivity of 69% is obtained.

By contrast, the yield of 2,4,6-trimethylquinol when using $Na_2MoO_4$ after 1 h is merely 24% and the selectivity 36%. When adding $Na_2MoO_4$ over 7 h, at best the yield of 2,4,6-trimethylquinol is 58% and the selectivity is 60%.

All values relating to FIG. 4 arise from gas chromatographic analyses of the respective reaction mixture and are expressed in percent by weight.

As already mentioned above, the concentration of the $H_2O_2$ used plays a minor role for the amount of 2,4,6-trimethylquinol produced and for the selectivity with which this compound is obtained.

In order to investigate this, in accordance with examples 13 to 15, 2.5 g (18.4 mmol) of mesitol are introduced as initial charge in 30 ml of methanol and admixed with 0.75 g (18.8 mmol) of sodium hydroxide (NaOH). The resulting suspension is stirred until the sodium hydroxide (NaOH) has dissolved completely, which requires ca. 10 min. The resulting solution is admixed with 0.1 mole equivalents of bismuth compound, the mole equivalents being based on the mesitol starting material. 21 g (185.3 mmol) of $H_2O_2$ are then added to the reaction mixture at room temperature over the course of 1 h, although this time the hydrogen peroxide ($H_2O_2$) is a 30% strength by weight solution and not a 50% strength by weight solution in water. The pale yellow suspension is then stirred for a further 12 h at room temperature and the reaction mixture is analyzed by means of gas chromatography.

Comparing examples 5 and 13, and 8 and 14 and in for example also 11 and 15, it is evident that equally good results are obtained using a 30% strength by weight solution of $H_2O_2$ as using a 50% strength by weight solution. Consequently, as stated above, the process procedure is largely independent of the concentration of the $H_2O_2$ and thus clearly superior to using molybdo and/or molybdate compounds. This is because the latter have a tendency, in the case of highly concentrated $H_2O_2$ solutions or when adding large amounts of $H_2O_2$, to form a molybdate complex which is no longer able to release singlet oxygen $^1O_2$ from $H_2O_2$.

EXAMPLE 31

Finally, it was also investigated what influence the order of the addition of reactants has on the yield and the selectivity with regard to the product 2,4,6-trimethylquinol.

For this, 5.00 g (36.7 mmol) of mesitol is dissolved in 10 ml of methanol and this solution is drawn into a syringe, which is then filled with further methanol to a total volume of 23 ml (solution 1). In a flask, 2.1 g (37.43 mmol) of potassium hydroxide (KOH) are dissolved in 60 ml of methanol, and 1.71 g (3.67 mmol) of bismuth oxide $Bi_2O_3$ are added. This mixture is stirred for 5 min, giving solution 2. To this is then added dropwise at the same time the prepared solution 1 and 25 g (367.7 mmol) of a 50% strength by weight hydrogen peroxide solution by means of an injection pump over the course of 1 h, during which it is ensured that the reaction temperature does not exceed 32° C. This mixture is then stirred overnight at room temperature and the reaction mixture is analyzed by means of gas chromatography.

Under these conditions, the yield of 2,4,6-trimethylquinol is 30% and the selectivity with regard to this compound 46%. This signifies a drop in yield and selectivity compared with the values given in tab. 1 and shows that the order with which reactants are mixed together has an influence on the yield according to the process of the invention.

In FIG. 5 it is seen that with the inventive bismuth compounds, large amounts of singlet oxygen $^1O_2$ can be released from $H_2O_2$ and, during the reaction with mesitol, these lead to high conversions of starting material coupled with simultaneously high selectivity for 2,4,6-trimethylquinol. Molybdo compounds and lanthanum compounds are clearly inferior here since although at best they bring about high conversions of mesitol, they produce the compound 2,4,6-trimethylquinol much less selectively.

However, the inventive process is not limited to one of the embodiments described above, but can be modified in diverse ways. For example, in accordance with the process it is possible to oxidize not only mesitol, but also compounds which are selected from the group 2-butene, isobutene, 2-methyl-1-butene, 2-hexene, 1,3-butadiene, 2,3-dimethylbutene, $\Delta_{9,10}$-octalin, 2-phthalimido-4-methyl-3-pentene, 2,3-dimethyl-1,3-butadiene, 2,4-hexadiene, 2-chloro-4-methyl-4-pentene, 2-bromo-4-methyl-3-pentene, 1-trimethylsilylcyclohexene, 2,3-dimethyl-2-butenyl paratolyl sulfone, 2,3-dimethyl-2-butenyl para-tolyl sulfoxide, N-cyclohexenylmorpholine, 2-methyl-2-norbornene, terpinols, α-pinene, β-pinene, ocimene, geraniol, farnesol, terpinene, limonene, trans-2,3-dimethylacrylic acid, α-terpinene, isoprene, cyclopentadiene, 1,4-triphenylbutadiene, 2-ethoxybutadiene, 1,1'-dicyclohexenyl, cholesterol, ergosterol acetate, 5-chloro-1,3-cyclohexadiene, 3-methyl-2-buten-1-ol, 3,5,5-trimethylcyclohex-2-en-1-ol, phenol, 1,2,4-trimethoxybenzene, 2,3,6-trimethylphenol, 1,4-dimethylnaphthalene, furan, furfuryl alcohol, furfural, 2,5-dimethylfuran, isobenzofuran, 2,3-dimethylindole, dibenzyl sulfite, (2-methyl-5-tert-butyl)phenyl sulfite etc.

In a process for the oxidation of mesitol with singlet oxygen which is released from hydrogen peroxide, this release takes place in the presence of a bismuth compound as catalyst. This produces 2,4,6-trimethylquinol in high yield and selectivity as product which can be used in further reactions for the synthesis of vitamins and in particular of vitamin A and vitamin E.

We claim:

1. A process for the oxidation of mesitol with singlet oxygen, which is released from $H_2O_2$, wherein the release is effected with a bismuth compound as catalyst wherein, the bismuth compound is selected from the group of bismuth oxides and/or bismuth nitrates and/or bismuth nitrate oxides and/or bismuth cobalt zinc oxide (Bi—Co—Zn—O) and/or bismuth citrate and/or from a mixture of these compound groups or compounds.

2. The process according to claim 1, wherein the mesitol is introduced as initial charge in a water-miscible solvent.

3. The process according to claim 2, wherein the mesitol is introduced as initial charge in a lower alcohol having 1 to 6 carbon atoms as solvent.

4. The process according to claim 2, wherein the solvent is rendered alkaline with a base.

5. The process according to claim 4, wherein the solvent is rendered alkaline with the base, comprising an aqueous solution of an alkali metal or alkaline earth metal hydroxide and/or an alcoholate and/or a hydride.

6. The process according to claim 4, wherein the solvent is rendered alkaline with the base, where further reactants are only added after the base has completely dissolved.

7. The process according to claim 4, wherein the base is added in a molar ratio which corresponds to 0.1 to 10-fold the molar amount of the mesitol.

8. The process according to claim 4, wherein the base is brought into solution mechanically.

9. The process according to claim 4, wherein the bismuth compound is added to the alkaline solvent comprising mesitol.

10. The process according to claim 1, wherein, per mole equivalent of bismuth compound, between 1 and 50 molar equivalents of mesitol are used.

11. The process according to claim 4, wherein $H_2O_2$ is added to the alkaline solvent comprising mesitol and bismuth compound.

12. The process according to claim 4, wherein, per mole equivalent of mesitol, a 2 to 70-fold molar excess of $H_2O_2$ is added to the alkaline solvent.

13. The process according to claim 1, wherein the $H_2O_2$ has a concentration of 5 to 60 wt % in water.

14. The process according to claim 4, wherein the $H_2O_2$ is added to the alkaline solvent comprising mesitol and bismuth compound over a period of from 30 minutes to 14 hours.

15. The process according to claim 4, wherein the $H_2O_2$ is added to the alkaline solvent continuously.

16. The process according to claim 2, wherein the $H_2O_2$ is added at a temperature of the solvent of from 0 to 90° C.

17. The process according to claim 1, wherein the molar ratio between bismuth compound and $H_2O_2$ is between 1:20 and 1:400.

18. The process of claim 1, wherein the oxidized mesitol is used for the production of 2,3,6-trimethylhydroquinone.

19. The process of claim 1, wherein the oxidized mesitol is used for the production of vitamin E.

* * * * *